May 23, 1972
W. H. JESSEL, JR., ET AL
Plant Pat. 3,185
CHRYSANTHEMUM PLANT
Filed July 27, 1970
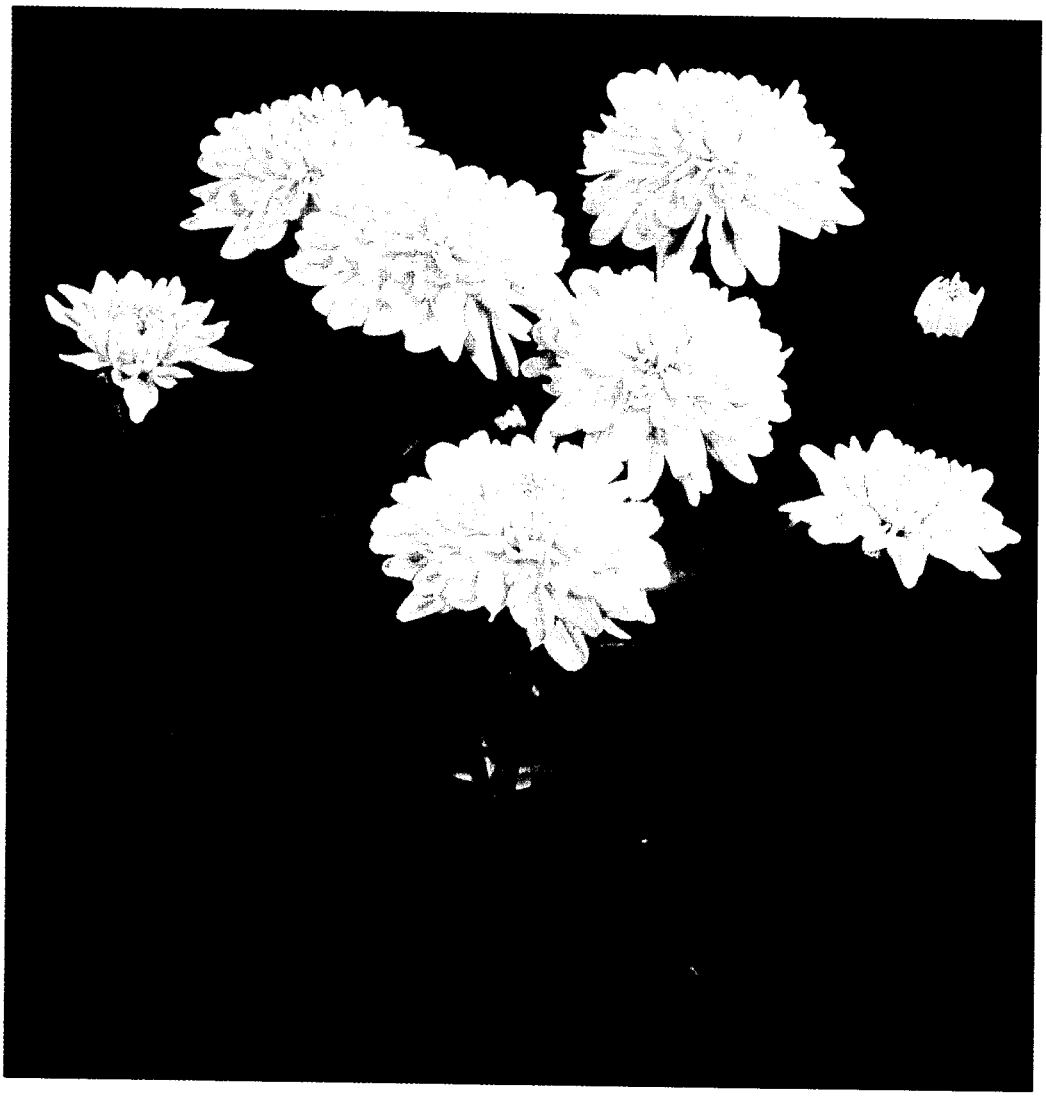
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,185
Patented May 23, 1972

3,185
CHRYSANTHEMUM PLANT

Walter H. Jessel, Jr., Doylestown, and William E. Duffett, Akron, Ohio, assignors to Yoder Brothers, Inc., Barberton, Ohio

Filed July 27, 1970, Ser. No. 58,751
Int. Cl. A01h *5/00*
U.S. Cl. Plt.—79 1 Claim

The present invention comprises a new and distinct variety of pompon chrysanthemum plant which is a sport of a light pink seedling identified for breeding purposes as YB 63340–1.

The new variety is similar in many respects to Bronze Belair, a commercial variety of Yoder Brothers, Inc., Barberton, Ohio, for which application for U.S. Letters Patent is concurrently being made. These similar characteristics are:

(1) Foliage size, shape, color.
(2) Nine week response.

The new variety is distinguished from Bronze Belair by the following characteristics:

(1) A flower ½" larger.
(2) Three days later response.
(3) Two to three inches more vigor.
(4) A more golden color, which changes from a golden orange-bronze to a golden yellow as temperatures increase.

The new variety is distinguished from Bronzechip, an unpatented but well established commercial variety of Yoder Brothers, Inc., by the following characteristics:

(1) Greater flower production, with trait to lateral flowering down the stem.
(2) Foliage less serrated.
(3) Spray formation more open and terminal.
(4) Better breaking action on a pinch, especially during high temperature periods.
(5) A flower ½" larger.

The new variety was discovered upon examination of a flowering plot of the parent variety.

My new variety has been asexually reproduced by cuttings at Barberton, Ohio, and has been found to retain its distinctive characteristics through successive propagations.

My new variety when grown in the vicinity of Salinas, Calif.; Fort Myers, Fla., and Barberton, Ohio has a response period of approximately 9 weeks. However, this response is approximately three days later than Bronze Belair in all periods of the year. It will be understood that the response time and blooming period may vary significantly with varying environmental conditions such as temperature, light intensity and day length. Suggested flowering in the northern United States is from April through November, and for southern Florida, from December through April.

The accompanying drawing shows the color and form of my new variety, the colors being as true as possible with color illustrations of this type.

The following is a detailed description of my new variety, with color references being to the Munsell Color Chart, 1963 Edition and comparisons made with the variety Bronze Belair.

Botanical classification: *Chrysanthemum morifolium.*

| | Golden Belair | Bronze Belair |
|---|---|---|
| Bloom: | | |
| Size | 3" | 2½". |
| Fully expanded | 3½" | 3". |
| Borne | Terminal cluster of 8–12 on elongated pedicel according to culture. | 3". |
| Stems | Elongated pedicels | 3". |
| Form | Decorative | 3". |
| Permanence | 7–10 days | 3". |
| Color: | | |
| Center of flower. | Orange-yellow ranging from 8.75YR 6/12–8 to 75YR7/12. | Orange-bronze ranging from 2.5YR 5/10 to 10YR8/10 light bronze. |
| Base of petals | Yellow, 3.75Y8/12 | Bronze 2.5YR5/10. |
| Inside of petals | Yellow, 2.5Y8/10 to yellow 1.25YR8/14. | Light bronze, 2.5YR 5/10 to 10YR8/10. |
| Reverse of petals. | Yellow, 2.5Y8.5/10 | Light yellow, 2.5Y8.5/6. |
| Tonality from a distance. | Gold bronze, gold yellow. | Orange bronze to light bronze. |
| Discoloration | Yellow, 1/25YR8/14 | Light bronze, 10YR 8/10. |

*Petals.*—Texture—smooth; appearance—slightly open at base, keeled at mid point, tapering to a blunt point; arrangement—composite whorled on a single receptacle; persistence—shatter resistant; fragrance—typical chrysanthemum.

*Reproductive organs.*—Stamens, anthers—none to 20, depending on culture; pollen—none to scant; arrangement—center of flower if present; styles—present in both ray and disc floret; length—short; ovaries—at base of petals attached to receptacle.

*Plant.* — Form — herbaceous;; growth — upright; height—38"–44", depending on culture; (Bronze Belair—36"–42", depending on culture).

*Foliage.*—Top side—green—7.5GY3/4; size—7"–9" long including petiole, 4"–5" wide; quantity—numerous; shape—palmate; texture—coarse; ribs and veins—prominent; edge—deeply indented; serration—slight; underside—light green—.5GY4/4; stipules—prominent at base of petiole.

I claim:

1. A new and distinct variety of pompon chrysanthemum characterized particularly as to novelty by a unique golden-bronze color, a relatively larger flower, increased flowers produced per stem, with an open terminal spray, lateral flowering down the stem, a superior breaking action, especially during high temperature periods, and a uniform, early response.

No references cited.

ROBERT E. BAGWILL, Primary Examiner

UNITED STATES PATENT OFFICE

CERTIFICATE OF CORRECTION

Patent No. PP 3,185 Dated May 23, 1972

Inventor(s) Walter H. Jessel, Jr. and William E. Duffett

It is certified that error appears in the above-identified patent and that said Letters Patent are hereby corrected as shown below:

In column 2, line 12 opposite Borne; line 13 opposite Stems; line 14 opposite Form and line 15 opposite Permanence delete 3" under Bronze Belair in each line.

In column 2, approximately line 17, adjacent the heading "Center of Flower" and under "Golden Belair", "6/12-8" should read --6/12--; and "75" should read --8.75--.

In column 2, approximately line 23, adjacent the heading "Tonality from a distance" and under "Golden Belair", "Gold bronze, gold yellow" should read --Gold bronze to gold yellow--.

In column 2, approximately line 24, adjacent the heading "Discoloration" and under the heading "Golden Belair", "1/25YR8/14" should read --1.25YR8/14--.

In column 2, line 44, ".5GY4/4" should read --7.5GY4/4--.

Signed and sealed this 2nd day of October 1973.

(SEAL)
Attest:

EDWARD M.FLETCHER,JR.
Attesting Officer

RENE D. TEGTMEYER
Acting Commissioner of Patents